United States Patent
Fossel

(10) Patent No.: US 6,207,713 B1
(45) Date of Patent: Mar. 27, 2001

(54) TOPICAL AND ORAL DELIVERY OF ARGININE TO CAUSE BENEFICIAL EFFECTS

(76) Inventor: Eric T. Fossel, 17 Sunset View Rd., S. Hero, VT (US) 05486

(*) Notice: Subject to any disclaimer, the term of this patent is extended or adjusted under 35 U.S.C. 154(b) by 0 days.

(21) Appl. No.: 08/936,189

(22) Filed: Sep. 17, 1997

(51) Int. Cl.$^7$ ............ A61K 31/195; A61K 6/00; A61K 9/127; A61K 47/00
(52) U.S. Cl. ............ 514/565; 424/401; 424/450; 424/439
(58) Field of Search .................. 424/401, 445, 424/446, 449, 463; 514/565

(56) References Cited

U.S. PATENT DOCUMENTS

| | | | |
|---|---|---|---|
| 5,595,753 | 1/1997 | Hechtman | 424/436 |
| 5,629,002 | 5/1997 | Weuffen | 424/401 |
| 5,891,459 | * 4/1999 | Cooke et al. | 424/439 |
| 5,925,372 | * 7/1999 | Berner et al. | 424/448 |

OTHER PUBLICATIONS

Cooper et al. The Transdermal Delivery of Drugs, vol. II, p 57–62, 1986.*

* cited by examiner

Primary Examiner—Theodore J. Criares
(74) Attorney, Agent, or Firm—Lorusso & Loud

(57) ABSTRACT

The use of orally administered L-arginine in conjunction with a topical preparation for producing enhanced blood flow in tissue thus causing beneficial effects such as warming cold tissue of the hands and feet, promoting hair growth on scalp tissue lacking sufficient hair, promoting healing of superficial ulcers such as leg ulcers in persons with diabetes, and overcoming male erectile failure (impotence) is disclosed. Specifically, use of orally administered L-arginine in conjunction with this is topical preparation provides local delivery of the amino acid L-arginine, an important biological precursor to the main substance which is responsible for relaxation of blood vessels permitting enhancement of blood flow. In the preferred embodiments, the L-arginine is provided so that it can be topically applied to the cold tissue. The preparation also contains an agent which aids in the transfer of L-arginine into the tissue. In the preferred embodiments this agent overcomes the resistance to transfer caused by the high charge density of L-arginine. In the preferred embodiments this means is high ionic strength created by addition of sodium chloride. This preparation, when topically applied to cold tissue, warming begins within 10 to 45 minutes and is sustained for periods as long as 2 to 18 hours. Further this preparation when applied nightly to scalp tissue lacking sufficient hair for a period of time causes substantial growth of hair on the scalp lacking sufficient hair, causes the healing of superficial ulcers such as leg ulcers and overcomes impotence.

11 Claims, No Drawings

TOPICAL AND ORAL DELIVERY OF ARGININE TO CAUSE BENEFICIAL EFFECTS

BACKGROUND

1. Field of the Invention

This invention relates to the use of L-arginine orally alone or in conjunction with topical application of a cream, gel, or other vehicle which contains substances such as L-arginine which delivers these substances into tissue for the purpose of producing beneficial effects such as warming of cold or cool tissues, growth of hair on the scalp, healing of leg ulcers secondary to diabetes or confinement to bed, relief of impotence, as well as beneficial effects through restoration of natural mechanisms based on improvement of local blood supply.

2. Prior Art

Approaches to improving local blood flow have been many and consist of both systemic and topical approaches. Many beneficial effects could be obtained should improvement in local blood flow be achieved since impairment of local blood flow causes a variety of negative consequences. Among these are cold hands and feet, lack of sufficient hair on the scalp, leg ulcers, certain forms of impotence, as well as a variety of other things. Approaches to warming cold tissue including cold hands, fingers, feet and toes constitute one section of the prior art. Many persons suffer from cold hands, feet or other body parts. This is often caused by insufficient blood flow in the cold tissue. Previously cold hands or feet have been treated by wearing warm socks or gloves, sometimes even socks or gloves which are mechanically heated. The use of hot packs and glove or shoe inserts which generate heat through chemical reactions has also been a potential solution. Certain liniments which are essentially irritants, such as those containing the red pepper derived substance, capsicum fall into this category. More recently, topical creams containing nitroglycerine have been used. See H. Natsuda et al., *Ryumachi* 34, 849 (1994). All of these approaches work at one level or another though are often extremely transient in nature. Nitroglycerine creams also have the disadvantage that nitroglycerine is a cardioactive drug, raising concerns of effects on the heart.

It has been recognized that deficiencies in blood flow in the scalp occur in male pattern baldness. See G. Duplechain et al., *J. Lousiana State Med Soc.* 146, 7 (1994); P Klemp et al., *J Invests Dermatol* 95, 725 (1989); S Toshitani et al., *J Dermatol* 17, 240 (1990). Topical minoxidil has been used as an agent for hair growth in male pattern baldness with varying results. Though the suggestion has been made that minoxidil operates through increase in the blood supply to the scalp, many investigators have failed to show such an effect See E de Boer et al., *Acta Dermato-Venereoligica* 68, 271 (1988); C Bunker et al., *British J Derm* 117, 668 (1987).

The fundamental fact that cold tissue of the hands, fingers, feet and toes as well as other cold tissue is caused by insufficient blood flow to the tissue has been suggested. It has further been suggested by some that the use of increased blood flow through relaxation of blood vessels, particularly small and very small vessels may be of use in warming cold tissue. However reasonable this suggestion, many attempts to demonstrate warming by use of agents which produce vasodilation and therefore increased blood flow have produced negative results. See N Dietz et al., *J Appl Physiol* 76, 2047 (1994); S Whitmore et al., *J Rheumatol* 22, 50 (1995); S Singh et al., *Eur J Clin Invest* 25, 182 (1995). The only report of modest temporary success involved the use of nitroglycerine. See H Natsuda et al., *Ryumachi* 34, 849 (1994). The use of the nitric oxide precursors such as L-arginine to produce warming secondary to vasodilation has been suggested. And a variety of indirect Dand non-definitive experiments have been conducted using oral administration. See M. Sonntag et al., *Pflugers Arch* 420, 194 (1992); A. Agostoi et al., *Int J Clin Lab Res* 21, 202 (1991). Thus, while the literature contains suggestions that vasodilation by administration of oral L-arginine, the precursor of nitric oxide (endothelium-dependent relaxing factor), no reports exist of success in producing warming of tissue using this agent. In fact Dietz (see N Dietz et al., *J Appl Physiol* 76,2047 (1994)) concludes from his data that "These data suggest that NO (nitric oxide) does not play a major role in cutaneous vasodilation during body heating in humans." Further Singh (see S Singh et al., *Eur J of Clin invest* 25, 182 (1995)) in a study of patients with Raynaud's phenomenon (severely cold hands and/or feet) concludes that L-arginine failed to cause vasodilation (and therefore warming) in patients with Raynaud's phenomenon.

The literature contains no suggestions or examples of the use of L-arginine in any mode of administration for the growth of hair in male pattern baldness or healing of ulcers of the skin.

It has long been recognized that impaired blood flow to the penis is a major cause of erectile failure (impotence) in men. See A Moradian et al. *Am J. Med* 85, 748, (1988); T Hwang et al. *J Formosan Med Assoc* 89, 992(1990). Further it has been recognized by using isolated tissue in vitro and in animal experiments that nitric oxide is an important mediator of relaxation of the vessels in penile cavernous tissue. See H Kirkeby et al. *Acta Physiol Scand* 149, 385 (1993). Topical nitroglycerine has been used in the treatment of impotence because of its ability to dilate vessels. The results were inconclusive and the treatment not well tolerated because of the cardiac response to nitroglycerine. See S Negelev *J Urology* 143, 586 (1990).

It was discovered that topical application of the nitric oxide precursor, L-arginine, in its various forms including orally alone or in conjunction with a variety of topical preparations, either by themselves or with other agents to aid in penetration such as a high ionic strength environment, neutralization of its charge in a complex or by other means, or included in a liposome or other biological carrier, when administered to cold or cool tissue causes a substantial and prolonged warming effect in the tissue, grow hair on hair-depleted scalp, facilitate healing of superficial ulcers such as leg ulcers and overcome impotence in many subjects.

In accordance with that invention, oral arginine by itself or in combination with a penetrating cream containing L-arginine at a concentration sufficient to produce an effect and sodium chloride or other salt at a concentration sufficient to create a hostile biophysical environment for the L-arginine in the cream is applied to the cold or cool tissue alone and/or in conjunction with oral arginine, exerts a warming effect which is prolonged, often lasting from 2–18 hours. In persons with very cold tissue (for example 22° C.) this warming effect can have a magnitude of 10° C. or more.

Further, in accordance with this invention, oral L-arginine alone or in conjunction with a penetrating cream containing L-arginine in a concentration sufficient to produce the desired effect along with sodium chloride or other salts at a concentration sufficient to produce a hostile biophysical environment when applied to bald areas of the scalp nightly either alone and/or in conjunction with oral arginine, produced growth of new hair within one month and substantial growth of hair within 3–4 months.

Yet further, in accordance with this invention, oral arginine alone or in conjunction with a penetrating cream containing L-arginine in a concentration sufficient to produce the desired effect along with sodium chloride or other salts at a concentration sufficient to produce a hostile biophysical environment when applied locally as the cream directly to the penis either alone and/or in conjunction with oral arginine, was effective in overcoming impotence.

Consequently, with the discovery of the present invention, a means to warm cold and cool tissue, a problem shared by many, was developed for improving this uncomfortable and often painful problem in human health has been found. Further with the discovery of the present invention, a means to restore hair growth on a bald portion of scalp has been found. Still further, with the discovery of the present invention, a means effect healing of superficial ulcers such as leg ulcers has been found. Yet further, with the discovery of the present invention, a means to overcome impotence in many men has been found.

These and other objects and features of the present invention will become apparent to those skilled in the art from reading the description of the invention, which follows.

SUMMARY OF THE INVENTION

Accordingly, several objects and advantages of the instant invention are to warm cold tissue in hands, feet or other tissue by increasing blood flow in the tissue means of enhancement of the body's natural mechanisms. It is further an object and advantage of the instant invention to prophylactically prevent tissue from becoming cold by use prior to entering into situations which induce cold hands and feet such as skiing or other winter outdoors activities. It is further an object and advantage of the instant invention to induce the growth of hair on portions of human scalp deficiency in hair by means of enhancement of the body's natural mechanisms. It is yet another object of the instant invention to induce healing of superficial ulcers of the limbs by means of enhancement of the body's natural mechanisms. It is still further another object of the instant invention to provide a means for overcoming impotence in many men.

In preferred embodiments, the oral delivery vehicles are capsules or tablets containing L-arginine used alone or in conjunction with a topical delivery vehicle such as a penetrating cream. In the cream the L-arginine is present as L-arginine hydrochloride in a concentration sufficient to produce the desired effect and the agent which creates the hostile biophysical environment is sodium chloride at a concentration sufficient to aid in tissue absorption.

PREFERRED EMBODIMENTS

The preferred embodiment uses tablets or capsules containing 200–500 mg of L-arginine to be used alone or in conjunction with a base cream with the properties of excellent absorption into the skin which also contains L-arginine hydrochloride (12.5% w/v), choline chloride (10%l w/v), magnesium chloride (5% w/v) and sodium chloride (5% w/v). The components of the base cream may be those commonly found in hand creams. The purpose of L-arginine hydrochloride is to provide a precursor to the molecule, nitric oxide, NO. The purpose of the sodium chloride is to provide a high ionic strength environment for the highly charged molecule, L-arginine. The base cream containing L-arginine and sodium chloride is the agent which is applied to the hands and/or feet to produce to produce a warming effect in the tissue, to produce hair growth or to effect healing of ulcers such as leg ulcers, or directly to the penis in order to aid in overcoming impotence.

The treatment consisting of oral administration of capsules or tablets containing L-arginine used alone or in conjunction with the cream acts effectively to warm cold tissue such as hands, fingers, feet, toes or other tissue when applied to the tissue and rubbed into the tissue to assure maximal absorption. The warming effect, caused by increased blood flow in the tissue is not instant but begins within 5 to 20 minutes. The effect is long lasting. Often the tissue remains warm for more than 2 to 18 hours. The treatment consisting of oral administration of capsules or tablets containing L-arginine used alone or in conjunction with the cream acts effectively to induce hair growth on bald human scalp when applied nightly to the bald area each night for several months. Hair growth is naturally a slow process. However, substantial hair growth is achieved over large areas of scalp with results becoming evident in a few weeks and substantial within several months. The cream further acts to promote healing of superficial ulcers such as those sometimes found on the legs of persons with severe diabetes. Application twice dally for a period of two weeks causes substantial healing and in many cases complete healing is achieved within this time period or slightly longer (3–4 weeks). Further the treatment consisting of oral administration of L-arginine used alone or in conjunction with the cream when carried out daily for a period of 7–10 days and then maintained with daily administration causes substantial relief from impotence in many men.

OTHER EMBODIMENTS

Other active agents

While L-arginine hydrochloride is the preferred active agent because it is the agent in nature itself, it is non-toxic, is highly soluble and it is inexpensive, other agents could be used which are also precursors or donors of nitric oxide. These include the salt, arginine glutamate, the salt, arginine butyrate, and esters of arginine such as arginine ethyl ester or arginine butyl ester as well as other donors of nitric oxide.

In the case an alternative active agent were used it would be simply substituted for L-arginine in a delivery preparation and the preparation used as in the case of the L-arginine preparation.

Other means of effecting absorption

A variety of means for effecting absorption of the active agent from the topical cream might be envisioned. One principle behind the absorption of a highly charged molecule such as L-arginine into tissue is to either create a biophysically hostile environment in the delivery vehicle such that L-arginine would prefer to be in tissue, or to package L-arginine in such a way that it is carried into tissue or neutralize its charge by derivitization or forming a neutral salt. Examples of biophysically hostile environments, include but are not limited to, high ionic strength, high or low pH, and highly hydrophobic environments. Examples of packaging which would be carried into tissue includes liposomes or emulsions of collagen, collagen peptides or other components of skin or basement membrane. Examples of neutralization of charge include the salt, arginine glutamate which is electronically neutral.

In each case of creating a hostile biophysical environment for the active agent, the agent was added to an appropriate preparation. In the case of creating a high ionic strength ions such as but not limited to sodium chloride, potassium chloride, choline chloride, magnesium chloride, lithium chloride, alone or in combination were added in high concentration. Other highly charged molecules such as polylysine, polyglutamine, polyaspartate or copolymers of such charged amino acids may be used to create the hostile biophysical environment. Alternatively a hostile biophysical environment may be created by placing the highly charged L-arginine in an hydrophobic, oily environment such as in an oil-based cream containing little or no water. Absorption may further be aided by combining the use of hostile biophysical environments with the use of penetrating agents such as oleoresin capsicum or its constituents or molecules containing heterocyclic rings to which are attached hydrocarbon chains.

EXAMPLE 1

In this example a person (female, age 52) with very cold fingers was provided with the above warming cream consisting of a delivery vehicle of penetrating cream, L-arginine hydrochloride (12.5% w/v), magnesium chloride (5% w/v), choline chloride (10% w/v) and sodium chloride (5% w/v). The surface temperature of the subject fingers of the left hand varied from 21 to 24° C. The warming cream was applied through rubbing into the skin. Surface temperatures of each finger were measured each 15 minutes for the initial hour. At 15 minutes following administration of the warming cream the effect had begun to occur with surface temperatures or various fingers rising to 26 to 29° C. The maximal effect was reached by 45 minutes with surface temperatures of various fingers becoming 31 to 34° C. The effect was sustained at least 4 hours.

EXAMPLE 2

In this example a 53 year old man with a severely receding hairline as well as large "bald spot" on the top rear of his head was provided with a penetrating cream containing L-arginine hydrochloride (12.5% w/v), choline chloride (10% w/v), magnesium chloride (5% w/v) and sodium chloride (5% w/v). The cream was applied to the areas of the scalp lacking sufficient hair each night before going to bed and was rubbed in extensively for maximal absorption. New hair growth was noted within 2–3 weeks. Within 4 months the receding hairline (previously 4 cm of hairless scalp) had returned to normal and the "bald spot" previously more than 7 cm in diameter had been reduced to an area of less than 2 cm with even this area showing some new hair growth.

EXAMPLE 3

In a 54 year old man with a history of impotence administration of 1.5 g L-arginine daily in the form of oral capsules combined with twice daily (morning and evening) administration of a penetrating cream containing L-arginine hydrochloride (12.5% w/v), choline chloride (10% w/v), magnesium chloride (5% w/v) and sodium chloride (5% w/v) directly to the penis for 7 days brought initial relief from the symptoms of impotence and allowed the subject to resume normal sexual activity. This relief of symptoms was maintained by continuation of the treatment daily.

Accordingly, it can be seen that in the present invention I have provided a method and agents, which when applied to cold, and often painful tissue, an increase in skin temperature results through utilization of one of the body's own mechanisms for producing warmth. This effect is achieved by providing the biochemical substrate at the local site from which the controlling substance, nitric oxide, is produced. Nitric oxide causes increases in local blood flow which results in warming. Further, it can be seen that in the present invention I have provided a method and agents which when applied to scalp lacking sufficient hair causes hair growth through utilization of one of the body's own mechanisms. This effect is achieved by providing the biochemical substrate at the local site from which the controlling substance, nitric oxide is produced. Nitric oxide causes increases in local blood flow which enables the growth of hair. Still further it can be seen that in the present invention I have provided a method and agents which when applied to leg ulcers cause healing through use of the body's own mechanisms. Yet still further, it can be seen that in the present invention I have provided a method and agents which when applied to a person with impotence causes overcoming of impotence by use of the body's own mechanisms. This effect is achieved by providing the biochemical substrate at the local site from which the controlling substance, nitric oxide is produced. Nitric oxide causes increases in local blood flow allowing the body's own healing cells and substances to reach the ulcer site.

Although the description above contains many specificities, these should not be construed as limiting the scope of the invention but as merely providing illustrations of some of the presently preferred embodiments of this invention. Various other embodiments and ramifications are possible within this scope.

Thus the scope of the invention should be determined by the appended claims and their legal equivalents, rather than by the examples given.

What is claimed is:

1. A method of increasing local blood flow by delivering a nitric oxide releasing substance selected from a member of the group consisting of L-arginine, L-arginine salts and L-arginine derivatives comprising the step of orally administering to the body a delivery vehicle for the substance, said delivery vehicle containing an effective amount of the substance and a concentration of ionic salt, sufficient to create a hostile biophysical environment which causes the substance to migrate from the delivery vehicle to the skin where the substance is absorbed by the surrounding tissue.

2. The method of claim 1 wherein the delivery vehicle selected from the group consisting of capsules, tablets, and liquids containing the substance is orally administered to the body.

3. The method of claim 1 wherein the delivery vehicle comprising L-arginine in the range of 0.5–30 g/day is administered.

4. A method of increasing local blood flow by delivering a nitric oxide releasing substance selected from a member of the group consisting of L-arginine, L-arginine salts and L-arginine derivatives comprising the step of orally administering to the body a delivery vehicle for the substance, said delivery vehicle containing an effective amount of the substance and a concentration of ionic salt sufficient to create a hostile biophysical environment which causes the substance to migrate from said delivery vehicle to the surrounding tissue where it is absorbed in conjunction with the step of topically applying a topical delivery vehicle containing an effective amount of the substance and a concentration of ionic salt sufficient to create a hostile biophysical environment which causes the substance to migrate from the vehicle to the selected area of skin where the substance is absorbed by tissue.

5. The method of claim 4 wherein the topical delivery vehicle is selected from a member of the group consisting of topical creams, topical liquids, topical lotions and topical ointments.

6. The method of claim 4 wherein the topical delivery vehicle that is applied to the skin is hydrophobic.

7. The method of claim 4 wherein a transdermal patch containing the topical delivery vehicle is applied to the skin.

8. The method of claim 4 wherein a delivery vehicle that is orally administered comprises L-arginine (0.5–30 g/day), and the topical delivery vehicle that is applied to the skin comprises water (20–80%), mineral oil (3–18%), glyceryl stearate (0.5–12%), squalene (0.2–12%), cetyl alcohol (0.1–11%), propylene glycol stearate (0.1–11%), wheat germ oil (0.1–6%), glyceryl stearate (0.1–6%), isopropyl myristate (0.1–6%), stearyl stearate (0–6%), polysorbate 60 (0.1–50%), propylene glycol (0.05–5%), tocopherol acetate (0.05–5%), collagen (0.05–5%), sorbitan stearate (0.5–5%), vitamin A&D (0.02–4%), triethanolamine (0.01–4%), methylparaben (0.01–4%), aloe vera extract (0.01–4%), imidazolidinyl urea (0.01–4%), propylparaben (0.01–4%), bha (0.01–4%), L-arginine hydrocholide (0.25% to 25%), sodium chloride (0.25% to 25%), and magnesium chloride (0.25% to 25%).

9. The method of claim 8 wherein the topical delivery vehicle further comprises choline chloride (0.25–25%).

10. The method of claim 8 wherein the topical delivery vehicle further comprises L-arginine glutamate (0.25–25%).

11. A method of increasing local blood flow by delivering a nitric oxide releasing substance selected from a member of the group consisting of L-arginine, L-arginine salts and L-arginine derivatives comprising the step of orally administering to the body a delivery vehicle for the substance, said delivery vehicle containing an effective amount of the substance and a concentration of ionic salt sufficient to create a hostile biophysical environment which causes the substance to migrate from said delivery vehicle to the surrounding tissue where it is absorbed, in conjunction with the step of topically applying a topical delivery vehicle containing an effective amount of the substance within a liposome, so that the liposome containing the substance migrates from the delivery vehicle into the skin where the substance is absorbed by tissue.

* * * * *